(12) United States Patent
Narusawa

(10) Patent No.: US 11,641,899 B2
(45) Date of Patent: May 9, 2023

(54) GARMENT FOR MEASURING BIOLOGICAL INFORMATION

(71) Applicant: TOYOBO CO., LTD., Osaka (JP)

(72) Inventor: Haruhiko Narusawa, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 576 days.

(21) Appl. No.: 16/617,758

(22) PCT Filed: May 24, 2018

(86) PCT No.: PCT/JP2018/020017
§ 371 (c)(1),
(2) Date: Nov. 27, 2019

(87) PCT Pub. No.: WO2018/221375
PCT Pub. Date: Dec. 6, 2018

(65) Prior Publication Data
US 2020/0178623 A1   Jun. 11, 2020

(30) Foreign Application Priority Data

May 29, 2017   (JP) .............................. JP2017-105415

(51) Int. Cl.
| | |
|---|---|
| *A41D 31/18* | (2019.01) |
| *A41D 31/26* | (2019.01) |
| *A41D 13/12* | (2006.01) |
| *A61B 5/25* | (2021.01) |
| *A61B 5/291* | (2021.01) |
| *A61B 5/296* | (2021.01) |
| *A61B 5/256* | (2021.01) |
| *A61B 5/27* | (2021.01) |
| *A61B 5/00* | (2006.01) |

(52) U.S. Cl.
CPC ....... *A41D 31/185* (2019.02); *A41D 13/1281* (2013.01); *A41D 31/26* (2019.02); *A61B 5/25* (2021.01); *A61B 5/256* (2021.01); *A61B 5/291* (2021.01); *A61B 5/296* (2021.01); *A61B 5/27* (2021.01); *A61B 5/6804* (2013.01)

(58) Field of Classification Search
CPC .............................................. A61B 2562/0247
See application file for complete search history.

(56) References Cited

U.S. PATENT DOCUMENTS

| | | | | |
|---|---|---|---|---|
| 4,983,923 | A * | 1/1991 | Taniguchi .............. | G01N 27/60 324/454 |
| 2006/0094948 | A1 | 5/2006 | Gough et al. | |
| 2007/0089800 | A1 | 4/2007 | Sharma | |
| 2010/0210745 | A1 * | 8/2010 | McDaniel ................ | C09D 7/48 521/55 |
| 2013/0338472 | A1 | 12/2013 | Maciá Barber et al. | |
| 2014/0336538 | A1 * | 11/2014 | Simonsen ............ | A61B 5/1126 600/595 |
| 2015/0305677 | A1 | 10/2015 | Berg et al. | |
| 2015/0359485 | A1 | 12/2015 | Berg et al. | |
| 2016/0120470 | A1 * | 5/2016 | Bogdanovich ....... | A61B 5/0002 340/870.07 |

FOREIGN PATENT DOCUMENTS

| | | |
|---|---|---|
| JP | 63-64303 | 3/1988 |
| JP | 6-260296 | 9/1994 |
| JP | 9-215668 | 8/1997 |
| JP | 11-225977 | 8/1999 |
| JP | 2003-041459 | 2/2003 |
| JP | 4860155 | 1/2012 |
| JP | 2014-151018 | 8/2014 |
| JP | 2016-106877 | 6/2016 |
| JP | 2017-29692 | 2/2017 |

OTHER PUBLICATIONS

International Search Report dated Aug. 21, 2018 in International (PCT) Application No. PCT/JP2018/020017.
Office Action dated Oct. 20, 2021 in Chinese Application No. 201880035428.6, with English translation.
Notice of Reasons for Refusal dated Feb. 22, 2022 in corresponding Japanese Patent Application No. 2019-522171, with Machine Translation.
Office Action dated May 12, 2022 in corresponding Chinese Patent Application No. 201880035428.6, with machine English langue translation.
Office Action dated Oct. 21, 2021 in corresponding Taiwanese Patent Application No. 107118291, with machine English-language translation.
Decision of Rejection dated Aug. 5, 2022 in corresponding Taiwanese Patent Application No. 107118291, with machine English-language translation.
Office Action dated Oct. 31, 2022 in corresponding Taiwanese Patent Application No. 107118291, with machine English-language translation.
Extended European Search Report dated Feb. 2, 2021 in corresponding European Application No. 18810259.4.
European Office Action dated Jan. 19, 2023 in corresponding European Patent Application No. 18810259.4.

\* cited by examiner

*Primary Examiner* — Henry Tsai
*Assistant Examiner* — Juanito C Borromeo
(74) *Attorney, Agent, or Firm* — Wenderoth, Lind & Ponack, L.L.P.

(57) ABSTRACT

A garment for measuring biological information equipped with an electrode and wiring, with which noise can be prevented from being mixed in to the biological electric signals to be read, and with which a wearer feels less discomfort, even under dry condition while the garment is worn. Static electrical charge generated while the garment is worn is suppressed to decrease the noise in the biological electric signals to be read by selecting a combination of electrically insulating materials constituting the garment that have smaller gap of frictional electrostatic voltage, as well as using the electrode and wiring that are stretchy and have high conductivity even when being stretched to reduce discomfort while the garment is worn.

10 Claims, No Drawings

GARMENT FOR MEASURING BIOLOGICAL INFORMATION

TECHNICAL FIELD

The present invention relates to a garment for measuring biological information having a stretchy electrode contacted with biological body's skin surfaces to measure faint electrical signals generated by the biological body.

BACKGROUND ART

An adhesive pad electrode made from electrically conductive adhesive materials such as solid gel that is electrically conductive and soft (Patent Document 1), or a suction electrode consisting of a rubber bulb and an electrode (Patent Document 2) have been used to measure faint electrical signals in biological bodies such as brain waves, an electrocardiogram, and an electromyogram. Such electrodes are supposed to be used in the condition that an examinee is placed at rest while the electrodes are attached to the examinee's skin.

On the other hand, since it is required that the electrical signals are measured over an extended period of time in daily lives, a garment to which an electrode is attached is drawing attention. Instead of the adhesive pad electrode that may cause dropping or flowing of the gel or the suction electrode that may cause bulkiness or blood stasis, a new electrode attached to a garment has been invented. For example, an electrode combining a fabric electrode made by interweaving metallic conductive fibers such as stainless and an electrode a part of which is impermeable to water is offered, which can avoid the effect of electrical noise caused by such a fabric-based electrode by using the electrode partially impermeable to water to reduce electric resistance between sweaty skin and the electrode (Patent Document 3).

In addition, an electrode, the constitution of which is unique in adopting water-repellent and electrically insulated materials for the part to which a sensor is attached, is offered in the form that a garment and the part to which a sensor is attached is adjoined by stitches, which prevent deterioration of the electrical signals caused by electrical short even in the condition where the garment is wet with rain or sweat and may act as an electrolyte (Patent Document 4).

RELATED ART DOCUMENTS

Patent Documents

Patent Document 1: Japanese Unexamined Patent Publication No. H09-215668
Patent Document 2: Japanese Unexamined Patent Publication No. H11-225977
Patent Document 3: Japanese Patent No. 4860155
Patent Document 4: Japanese Unexamined Patent Publication No. 2016-106877

SUMMARY OF THE INVENTION

Problems to be Solved by the Invention

As described above, as a garment to which an electrode is attached to measure electrical signals over an extended period of time in daily lives, preventing electrical noise and deterioration of the electrical signals is necessary even though the garment is in a condition from dry condition to wet condition with rain or sweat, or a wearer makes various postures and movements. In addition, since the garment is worn over an extended period of time, the electrode is required to be stretchy and soft that enables it to follow the garment, in view of comfort of the garment such as reduction in rigid feeling and maintenance of fit feeling.

However, there has been a problem that when a conventional garment to which an electrode is attached is worn over an extended period of time, a phenomenon occurs that the electrical signals deteriorates because of noise especially in the dry condition. The present invention is developed focusing on such a phenomenon. Supposing that the noise results from frictional electrostatic voltage generated by rubbing the constituents together, and that the noise results from change in electrical characteristics when a wearer is making various postures and movements to make the electrode elongate and contract, the purpose of the present invention is to prevent the noise from being mixed into the electrical signals to degrade it even though a wearer makes various postures and movements in the dry condition.

Means for Solving the Problems

The present invention is as follows.

[1] A garment for measuring biological information, comprising:
a first stretchy electrically insulated base material substrate constituting the garment;
a second stretchy electrically insulated base material provided in proximity to the first stretchy electrically insulated base material; and
a stretchy electrically conductive material, wherein
an absolute value of frictional electrostatic voltage generated by rubbing the first stretchy electrically insulated base material and the second stretchy electrically insulated base material together is 10 kV or less.

[2] The garment for measuring biological information according to [1], wherein the stretchy electrically conductive material has a sheet resistance of 300Ω☐ or less when being not stretched; a load on the stretchy electrically conductive material when being stretched at a stretch rate of 10% is 100 N or less; and an increase rate of electric resistance of the electrically conductive stretchy material when being stretched is less than 10 times.

[3] The garment for measuring biological information according to [1] or [2], wherein the stretchy electrically conductive material comprises a stretchy electrically conductive sheet comprising at least electrically conductive particles and an electrically insulated binder resin.

[4] The garment for measuring biological information according to [1] or [2], wherein the stretchy electrically conductive material comprises a stretchy electrically conductive fabric comprising at least electrically conductive fibers.

[5] The garment for measuring biological information according to any one of [1] to [4], wherein the first stretchy electrically insulated base material is one or more fiber materials selected from cotton, wool, hemp, silk, polyester, polypropylene, polyamide, polyacrylamide, rayon, aromatic polyamide, and polybenzoxazole.

[6] The garment for measuring biological information according to any one of [1] to [5], wherein the second stretchy electrically insulated base material comprises an electrically insulated material comprising one or more of fluorine-based resins, polypropylene, polyethylene, polyurethane, polyacrylic acid, polystyrene, polyester, polyamide-imide, polyimide, natural rubber, synthetic rubber, or a combination thereof.

[7] The garment for measuring biological information according to any one of [1] to [4], wherein the first stretchy electrically insulated base material comprises a fiber material including 50% of cotton, and the second stretchy electrically insulated base material comprises an electrically insulated material comprising one or more of polyamide, polyurethane, polyester, nitrogen-containing synthetic rubber, or a combination thereof.

[8] The garment for measuring biological information according to any one of [1] to [4], wherein the first stretchy electrically insulated base material comprises a fiber material including 50% or more of polyester fibers, and the second stretchy electrically insulated base material comprises an electrically insulated material comprising one or more of polyacrylamide, polyacrylic acid ester, polyester, polyvinyl butyral, natural rubber, non-nitrogen-containing synthetic rubber, or a combination thereof.

The present invention preferably further comprises the following features.

[9] The garment for measuring biological information according to any one of [1] to [8], wherein the garment comprises a means of measuring biological information of a wearer thereof and a mechanism of transmitting the measured biological information to the outside of the garment.

[10] The garment for measuring biological information according to any one of [1] to [9], wherein the garment comprises a means of measuring biological information of a wearer thereof and a mechanism of analyzing the measured biological information.

[11] The garment for measuring biological information according to any one of [1] to [4], wherein an electrically insulated material constituting the first stretchy electrically insulated base material and the second stretchy electrically insulated base material comprises one or more of fluorine-based resins, polypropylene, polyethylene, polyurethane, acryl, polystyrene, polyester, rubber, or a combination thereof.

[12] The garment for measuring biological information according to any one of [1] to [4], wherein an electrically insulated material constituting the first stretchy electrically insulated base material and the second stretchy electrically insulated base material comprises one or more of nylon, rayon, wool, silk, cotton, or a combination thereof.

Effects of the Invention

According to the present invention, a garment of the present invention includes a first stretchy electrically insulated base material, a stretchy electrically conductive material, and a second stretchy electrically insulated base material provided in proximity to the first stretchy electrically insulated base material to laminate and/or join the first stretchy electrically insulated base material and the stretchy electrically conductive material. By selecting base materials and components to satisfy the following features: frictional electrostatic voltage generated by rubbing the first stretchy electrically insulated material and the second stretchy electrically insulated material together is 10 kV or less, the stretchy electrically conductive material has a sheet resistance of 300Ω☐ or less when being not stretched, a load on the electrically conductive stretchy material when being stretched at a stretch rate of 10% is 100 N or less, and an increase rate of electric resistance of the stretchy electrically conductive material when being stretched is less than 10 times; noise can be prevented from being mixed into the electrical signals to degrade it in any condition of a garment from dry condition to wet condition with rain or sweat while reducing rigid feeling and maintaining fit feeling while the garment is worn.

MODE FOR CARRYING OUT THE INVENTION

<First Stretchy Electrically Insulated Base Material>

A first stretchy electrically insulated base material used in the present invention has a specific volume resistivity of $10^{10}$ Ω·cm or more, and comprises one or more materials selected from natural materials or synthetic resin materials that can be stretched at a stretch rate of 10% or more, the form of which is knit fabric, woven fabric, or nonwoven fabric consisting of fibers; or molded products in the form of film or sheet. The base material preferably has a thickness of 100 μm to 1000 μm and a basis weight of 100 g/m$^2$ to 300 g/m$^2$. The thickness and the basis weight of the base material is appropriately selected according to rigid feeling and fit feeling while the garment is worn.

The first stretchy electrically insulated base material preferably comprises one or more fiber materials selected from cotton, wool, hemp, silk, polyester, polypropylene, polyamide, polyacrylamide, rayon, aromatic polyamide, and polybenzoxazole.

<Stretchy Electrically Conductive Material>

A stretchy electrically conductive material used in the present invention is used as an electrode reading electric biological information and/or wiring transmitting the electric information.

The stretchy electrically conductive material preferably used in the present invention is a stretchy electrically conductive sheet comprising at least electrically conductive particles and an electrically insulated binder resin. The electrically insulated binder resin is a stretchy polymer material, and has a specific volume resistivity of $10^{10}$ Ω·cm or more, and comprises one or more polymer materials selected from natural materials or synthetic resin materials that can be stretched at a stretch rate of 10% or more.

The electrically conductive particles comprise one or more materials selected from metal, carbon-based materials, electrically conductive polymer, the electric conductivity of which is 10 S/cm or more, the form of which is powder or fiber, and used in the condition where the electrically conductive particles are dispersed in the electrically insulated binder resin.

Another stretchy electrically conductive material preferably used in the present invention is a stretchy electrically conductive fabric comprising at least electrically conductive fibers. The electrically conductive fibers in the present invention include fibers of electrically conductive polymer, fibers of electrically conductive components, fiber materials coated with electrically conductive materials on the surface, and hybrid fiber materials of electrically conductive materials and electrically insulated materials. Such electrically conductive fibers can be used as it is, or used by being hybridized with electrically insulated fibers. The fabric includes either woven fabric or knit fabric. Especially, the knit fabric is preferably used in the present invention because it is elastic enough.

The stretchy electrically conductive material of the present invention preferably has a sheet resistance of 300Ω☐ or less when being not stretched, which is achieved by selecting the kind of materials and the thickness or width of the components. In a case where the sheet resistance is more than 300Ω☐, electric signals deteriorates and become difficult to be read.

A load on the electrically conductive stretchy material when being stretched at a stretch rate of 10% in the present invention is preferably 100 N or less, and an increase rate of electric resistance when being stretched at a stretch rate of 10% is less than 10 times. In a case where the load on the electrically conductive stretchy material when being stretched at a stretch rate of 10% is more than 100 N, the rigid feeling and the fit feeling deteriorate. In addition, in a case where the increase rate of electric resistance when being stretched at a stretch rate of 10% is 10 times or more, the electric signals obtained before and after being stretched fluctuate and deteriorate.

<Second Stretchy Electrically Insulated Base Material>

A second stretchy electrically insulated base material used in the present invention has a specific volume resistivity of $10^{10}$ Ω·cm or more, and comprises one or more materials selected from natural materials or synthetic resin materials that can be stretched at a stretch rate of 10% or more. The second stretchy electrically insulated base material is provided to laminate and/or join the first stretchy electrically insulated base material and the stretchy electrically conductive material.

The second stretchy electrically insulated base material of the present invention is preferably processed into any one of the following forms. The first preferable form is liquid, which is firstly coated on the first stretchy electrically insulated base material or the stretchy electrically conductive material, and subsequently, is dried or cured to laminate and/or join them. The second preferable form is molded products in the form of film or sheet, which is laminated on the first stretchy electrically insulated base material or the stretchy electrically conductive material, and subsequently, is heated to laminate and/or join them. The third preferable form is thread, which is used to stitch the first stretchy electrically insulated base material and the stretchy electrically conductive material to join them.

The second stretchy electrically insulated base material of the present invention preferably comprises one or more of fluorine-based resins such as polytetrafluoroethylene, polypropylene, polyethylene, polyurethane, polyacrylic acid, polystyrene, polyester, polyamideimide, polyimide, natural rubber, synthetic rubber, or a combination thereof. A material coated or surface treated with fluorine-based resins can be treated as the fluorine-based resins.

<Electrically Conductive Sheet>

The electrically conductive sheet is one form of the stretchy electrically conductive material. It is obtained by mixing stretchy electrically insulated material and electrically conductive powder material in the form of solution or molten state, and then uniformly dispersing the electrically conductive powder material in the stretchy electrically insulated material, which is subsequently molded into sheet form. The amount of the electrically conductive powder material in the electrically conductive sheet is determined in consideration of resistivity and stretching properties. While larger volume % of the electrically conductive powder material leads to lower resistivity to prevent deterioration of the electric signals, it leads to lower stretching properties to cause deterioration of the rigid feeling and the fit feeling. On the other hand, smaller volume % of the electrically conductive powder material leads to higher stretching properties to improve the rigid feeling and the fit feeling, however, it leads to higher resistivity to cause deterioration of the electric signals. Considering the balance between the both properties, the amount of the electrically conductive powder material is preferably 20% to 60% (v/v).

<Electrically Conductive Fabric>

The electrically conductive fabric is another form of the stretchy electrically conductive material, which is knit fabric, woven fabric, or nonwoven fabric containing the electrically conductive material in the form of fibers. The electrically conductive fabric may be a combination of electrically conductive fibers and electrically insulated fibers. The ratio of the electrically conductive fibers in the electrically conductive fabric is determined in consideration of resistivity and stretching properties. While larger weight % of the electrically conductive fibers leads to lower resistivity to prevent deterioration of the electric signals, it leads to lower stretching properties to cause deterioration of the rigid feeling and the fit feeling. On the other hand, smaller weight % of the electrically conductive fibers leads to higher stretching properties to improve the rigid feeling and the fit feeling, however, it leads to higher resistivity to cause deterioration of the electric signals. Considering the balance between the both properties, the ratio of the electrically conductive fibers is preferably 10% to 100% (w/w).

The present invention is characterized by a frictional electrostatic voltage of the first stretchy electrically insulated material and the second stretchy electrically insulated material of 10 kV or less. The both materials are positioned in proximity to each other, and from a microscopic viewpoint, they are microscopically rubbed with each other to generate the frictional electrostatic voltage, when a wearer who wears a garment including the materials is moving. As for the frictional electrostatic voltage, one material is positively charged and another material is negatively charged, and the voltage largely depends on the combination of the materials. Since a combination having larger gap of the voltage causes noise to be mixed into the electric signals to degrade it, it is preferable to select a combination each material of which has smaller gap of the voltage. While materials tending to negatively charged are exemplified by fluorine-based resins, polypropylene, polyethylene, polyurethane, acryl, polystyrene, polyester, and rubber; materials tending to positively charged are exemplified by nylon, rayon, wool, silk and cotton. It is preferable in the present invention to select a combination having a certain range of the electrostatic voltage among the above materials and a combination thereof. A material coated or surface treated with fluorine-based resins can be treated as the fluorine-based resins.

EXAMPLES

Hereinafter, the present invention is specifically described with reference to examples, however, the present invention is not limited by the following examples.

[Preparing Electrically Conductive Paste]

Using the materials shown in Table 1, the resin was dissolved in the solvent at the weight % shown in Table 2 to obtain a solution, to which silver particles were added, and then, the resultant was mixed with a triple roll mill to obtain electrically conductive paste.

TABLE 1

| Materials | Abbreviation | Substances |
|---|---|---|
| resin | CSM | chlorosulfonated polyethylene rubber CSM-TS530 manufactured by Tosoh Corporation |
| | DN3 | nitrile rubber Nipol DN003 manufactured by Zeon Corporation |
| | UR6 | polyester-urethane resin Vyron UR6100 manufactured by Toyobo Co., Ltd. |

TABLE 1-continued

| Materials | Abbreviation | Substances |
|---|---|---|
| solvent | CHX | cyclohexane |
| | IPH | isophorone |
| | SOL | solvesso |
| silver particles | G35 | aggregated silver powder G-35 manufactured by DOWA Electronics Materials Co., Ltd. |
| | FAD3 | flake-formed silver powder FA-D-3 manufactured by DOWA Electronics Materials Co., Ltd. |
| hot-melt sheet | NT | polyamide-based hot-melt Elphan NT manufactured by Nihon Matai Co., Ltd. |
| | UH | polyurethane-based hot-melt Elphan UH manufactured by Nihon Matai Co., Ltd. |
| shirt | Cotton | GUNZE inner-shirt Yawaraka Hadagi cotton 100% manufactured by Gunze Limited |
| | Polyester | Cool-One polyester 100% manufactured by Sanwa Co., Ltd. |

TABLE 2

| Item | | PS01 | PS02 | PS03 |
|---|---|---|---|---|
| resin | CSM | 20 | | |
| | DN3 | | 20 | |
| | UR6 | | | 20 |
| solvent | CHX | | | 15 |
| | IPH | | 45 | 10 |
| | SOL | 45 | | 20 |
| silver particles | G35 | 80 | 60 | 60 |
| | FAD3 | | 20 | 20 |
| thickness (μm) | | 92 | 96 | 104 |
| sheet resistance (Ω□) | | 121 | 66 | 41 |
| increase rate of resistance at a stretch rate of 10% | | 1.9 | 1.3 | 1.5 |
| load at a stretch rate of 10% (N/cm) | | 37 | 52 | 61 |

[Preparing Stretchy Electrically Conductive Materials]

The above electrically conductive paste was coated on a release-treated PET film with an applicator such that the dried film thickness is 100 μm, which was then dried in a hot-air-drying oven at 120° C. for 30 minutes. Subsequently, the release-treated PET film was released to obtain a sheet of stretchy electrically conductive material. With the means specified below, the thickness, the resistance when not stretched, the increase rate of resistance when stretched, and the load when stretched were measured. The results are shown in Table 2.

[Preparing Garments Equipped with an Electrode and Wiring]

The stretchy electrically conductive material sheet with the release-treated PET film prepared in the above procedures were laminated with the hot-melt sheet shown in Table 1 and release paper, which were joined with a roll laminator equipped with rubber rolls the temperature of which was set at 120° C. to obtain adhesive stretchy electrically conductive material sheet. The stretchy electrically conductive material sheet was cut into a square shape with a side length of 5.0 cm leading to wiring the width of which was 1.0 cm and the length of which was 15.0 cm. The release paper was released from the obtained electrode with the wiring, which was then placed on a predetermined position on the reverse side of a shirt (made of 100% of cotton, and 100% of polyester) and thermocompression bonded with an iron. Subsequently, the release-treated PET film was released to obtain the shirt having the electrode and the wiring on the reverse side.

[Preparing a Shirt Equipped with a Mechanism of Measuring Heart Rate]

A hook made of stainless steel was attached on the obverse side of the end of the wiring placed on the shirt with the electrode and the wiring so as to be electrically conductively connected with the wiring on the reverse side, through which a heat rate sensor WHS-2 manufactured by Union Tool Co. was connected to prepare a shirt equipped with a mechanism of measuring heart rate.

[Stretch Test and Measurement of Sheet Resistance]

The above prepared stretchy electrically conductive material sheet was pinched by chucks such that the gap between the chucks was 5.0 cm with a stretch test machine (hand-turned stretching machine) equipped with two chucks the width of which was 2.5 cm, and was stretched in the longitudinal direction until the stretch rate reached 10% (the amount of displacement was 0.5 cm). The sheet resistance before and after the stretch test was obtained by measuring resistance (Ω) before and after the stretch test between the outside of the two facing chucks (the measurement distance was 10 cm) with a digital multi-meter YOKOGAWA TY530 manufactured by Yokogawa Meter & Instruments Corporation to obtain the sheet resistance (Ω□). The resistance was measured immediately after stretching (within 3 seconds).

[Measurement of a Load when Stretched]

A load applied to the stretchy conductive material sheet, a test piece of which has the width of 30 mm and the length of 50 mm, when the sheet was stretched at the stretch rate was 10% was measured with a tensile tester RTM-250 manufactured by Orientec Corporation to obtain a unit load per the sheet length of 1 cm (N/cm).

[Measurement of Frictional Electrostatic Voltage]

Frictional electrostatic voltage was measured in accordance with electrostatic voltage attenuation measurement method of JIS L1094 with a Kanebo's Frictional Electrostatic Voltage Measuring System EST-8 under a temperature of 20° C. and a humidity of 40% RH. The hot-melt sheet, which corresponds to the second stretchy electrically insulated base material, was rubbed ten times with a piece of fabric made of 100% of cotton and 100% of polyester, which was a friction cloth and corresponds to the first stretchy electrically insulated base material, and subsequently, an initial electrostatic voltage was measured to obtain an absolute value. The results of Examples and Comparative Examples are shown in Table 3.

[Wear Comfort and S/N Ratio in Measurement of Electrocardiogram]

Examinees, which were 10 male adults, put on the shirt equipped with the mechanism of measuring heart rate prepared in the Examples, and performed radio gymnastic exercises 1 and successively radio gymnastic exercises 2, while their electrocardiogram was measured under the circumstance of 15° C. and 40% RH. Wear comfort during the examination was ranked on a scale of five, the best of which was point 5 meaning "good texture" and the worst of which was point 1 meaning "bad texture, and obtained the average point offered by 10 examinees to make an evaluation, in which the average point of 4 or more meant "excellent", the average point of 3 or more and less than 4 meant "good", the average point of 2 or more and less than 3 meant "fair", and the average point of less than 2 meant "poor".

Signal (S) was defined as amplitude dispersion of R wave of the electrocardiogram, and noise (N) was defined as amplitude dispersion of wave between R wave and R wave, except the ones obtained for one minute on the either side of the exercise time. According to the equation S/N, S/N ratio when measuring electrocardiogram was obtained. The results of Examples and Comparative Examples are shown in Table 3.

TABLE 3

|  | Example 1 | Example 2 | Example 3 | Example 4 | Comparative Example 1 | Comparative Example 2 |
|---|---|---|---|---|---|---|
| First stretchy electrically insulated base material | cotton | cotton | polyester | polyester | cotton | polyester |
| Second stretchy electrically insulated base material | NT (polyamide-based) | NT (polyamide-based) | UH (polyurethane | UH (polyurethane | UH (polyurethane | NT (polyamide-based) |
| Frictional electrostatic voltave (kV) | 7.2 | 7.2 | 6.8 | 6.8 | 14.0 | 20.0 |
| Stretchy electrically conductive material | PS01 | PS02 | PS02 | PS03 | PS02 | PS03 |
| Wear comfort | Good | Good | Good | Good | Good | Good |
| S/N ratio | 3.6 | 3.4 | 4.2 | 3.9 | 1.5 | 1.3 |

As described above, it can be understood that using a combination causing lower fractional electrostatic voltage generated by rubbing the first stretchy electrically insulated base material and the second stretchy electrically insulated base material allows good measurement of electrocardiogram with lower noise.

INDUSTRIAL APPLICABILITY

The present invention is to offer a garment for measuring biological information that allows good measurement even under the dry condition in winter, and can be used for health management in daily lives, grasping biological information during outdoor sports such as jogging and marathon, and labor management of outdoor work such as the one at a construction site.

The invention claimed is:

1. A garment for measuring biological information, comprising:
    a first stretchy electrically insulated base material constituting the garment;
    a second stretchy electrically insulated base material provided in proximity to the first stretchy electrically insulated base material; and
    a stretchy electrically conductive material, wherein
    an absolute value of frictional electrostatic voltage generated by rubbing the first stretchy electrically insulated base material and the second stretchy electrically insulated base material together is 10 kV or less;
    the stretchy electrically conductive material has a sheet resistance of 300Ω☐ or less when being not stretched;
    a load on the stretchy electrically conductive material when being stretched at a stretch rate of 10% is 100 N or less; and
    an increase rate of electric resistance of the stretchy electrically conductive material when being stretched is less than 10 times.

2. The garment for measuring biological information according to claim 1, wherein the stretchy electrically conductive material comprises a stretchy electrically conductive sheet comprising at least electrically conductive particles and an electrically insulated binder resin.

3. The garment for measuring biological information according to claim 1, wherein the stretchy electrically conductive material comprises a stretchy electrically conductive fabric comprising at least electrically conductive fibers.

4. The garment for measuring biological information according to claim 1, wherein the first stretchy electrically insulated base material is one or more fiber materials selected from the group consisting of cotton, wool, hemp, silk, polyester, polypropylene, polyamide, polyacrylamide, rayon, aromatic polyamide, and polybenzoxazole.

5. The garment for measuring biological information according to claim 1, wherein the second stretchy electrically insulated base material comprises an electrically insulated material comprising one or more of fluorine-based resins, polypropylene, polyethylene, polyurethane, polyacrylic acid, polystyrene, polyester, polyamideimide, polyimide, natural rubber, synthetic rubber, or a combination thereof.

6. The garment for measuring biological information according to claim 1, wherein the first stretchy electrically insulated base material comprises a fiber material including 50% of cotton, and the second stretchy electrically insulated base material comprises an electrically insulated material comprising one or more of polyamide, polyurethane, polyester, nitrogen-containing synthetic rubber, or a combination thereof.

7. The garment for measuring biological information according to claim 1, wherein the first stretchy electrically insulated base material comprises a fiber material including 50% or more of polyester fibers, and the second stretchy electrically insulated base material comprises an electrically insulated material comprising one or more of polyacrylamide, polyacrylic acid ester, polyester, polyvinyl butyral, natural rubber, non-nitrogen-containing synthetic rubber, or a combination thereof.

8. The garment for measuring biological information according to claim 1, wherein each of the first stretchy electrically insulated base material and the second stretchy electrically insulated base material independently comprises at least one selected from the group consisting of fluorine-based resins, polypropylene, polyethylene, polyurethane, acryl, polystyrene, polyester, rubber, and a combination thereof.

9. The garment for measuring biological information according to claim 1, wherein each of the first stretchy electrically insulated base material and the second stretchy electrically insulated base material independently comprises at least one selected from the group consisting of nylon, rayon, wool, silk, cotton, and a combination thereof.

10. A garment for measuring biological information, comprising:
- a first stretchy electrically insulated base material constituting the garment;
- a second stretchy electrically insulated base material provided in proximity to the first stretchy electrically insulated base material; and
- a stretchy electrically conductive material, wherein
- each of the first stretchy electrically insulated base material and the second stretchy electrically insulated base material independently comprises at least one selected from the group consisting of fluorine-based resins, polypropylene, polyethylene, polyurethane, acryl, polystyrene, polyester, rubber, and a combination thereof; or
- each of the first stretchy electrically insulated base material and the second stretchy electrically insulated base material independently comprises at least one selected from the group consisting of nylon, rayon, wool, silk, cotton, and a combination thereof; and
- an absolute value of frictional electrostatic voltage generated by rubbing the first stretchy electrically insulated base material and the second stretchy electrically insulated base material together is 10 kV or less.

* * * * *